United States Patent [19]

Ismail

[11] Patent Number: 4,612,194

[45] Date of Patent: Sep. 16, 1986

[54] ANTI-RHEUMATIC AGENTS AND THEIR USE

[76] Inventor: Roshdy Ismail, Siebengebirgs-Apotheke, Siebengebirgsallee 2, 5000 Köln 41, Fed. Rep. of Germany

[21] Appl. No.: 700,462

[22] Filed: Feb. 11, 1985

[30] Foreign Application Priority Data

Feb. 15, 1984 [DE] Fed. Rep. of Germany ....... 3405240
Feb. 27, 1984 [DE] Fed. Rep. of Germany ....... 3407024
Mar. 7, 1984 [DE] Fed. Rep. of Germany ....... 3408260
Apr. 24, 1984 [DE] Fed. Rep. of Germany ....... 3415250
May 2, 1984 [DE] Fed. Rep. of Germany ....... 3416142
Aug. 7, 1984 [DE] Fed. Rep. of Germany ....... 3429019
Sep. 7, 1984 [DE] Fed. Rep. of Germany ....... 3432381
Sep. 7, 1984 [DE] Fed. Rep. of Germany ....... 3432832

[51] Int. Cl.$^4$ .................. A61K 31/05; A61K 31/35; A61K 31/41; A61K 31/44; A61K 31/52; A61K 31/135; A61K 31/355; A61K 31/435; A61K 31/495; A61K 31/505; A61K 35/78

[52] U.S. Cl. .................. 424/195.1; 514/255; 514/258; 514/265; 514/277; 514/288; 514/359; 514/456; 514/458; 514/646; 514/731

[58] Field of Search ............... 424/284, 195, 255, 258, 424/265, 277, 288, 359, 456, 458, 646, 731; 514/458

[56] References Cited

PUBLICATIONS

Chem. Abst. 83-193553c, (1975).
Chem. Abst. 89-117835e, (1978).
Chem. Abst.-99-4455u.

Primary Examiner—Stanley J. Friedman
Attorney, Agent, or Firm—Wegner & Bretschneider

[57] ABSTRACT

Anti-rheumatic agents contain vitamin E in combination with vasodilators and/or blood circulation-promoting agents. A method of treating rheumatic diseases is disclosed also.

6 Claims, No Drawings

ANTI-RHEUMATIC AGENTS AND THEIR USE

BACKGROUND OF THE INVENTION

The present invention relates to a new use of vitamin E.

Vitamin E is known as an antioxidant and protective vitamin for phospholipids of the cell membrane. Vitamin E maintains the permeability and stability of the cell membrane; cf. Lucy, Annals N.Y. Academy of Science 203, p. 4 (1972). It is further known that vitamin E has a membrane-sealing effect; cf. F. Mittelbach and G. Bodechtel, Münchner Medizinische Wochenschrift 110 (1968) 36: pp. 1988-1993. Vitamin E has also been found to provide a protective effect for the cell membrane in erythrocytes, the simplest cells of the human body. In both animal and human tests, it has been proven that anemia is a first signal of a vitamin E deficiency. The hemolysis of the erythrocytes will normalize upon administration of high does of vitamin E; cf. William J. Darbey Vitamin Horm., 26 (50) pp. 685-704 (1968) and Phelps DL Pediatrics 63 (6) pp. 933-935 (1979). From these literature references, it is apparent that, after the oral administration of from 200 to 800 mg of vitamin E over a period of from 1 to 4 days, the hemolysis of the erythrocytes is significantly improved as compared to erythrocytes hemolysis in those patients suffering from vitamin E dificiency.

Vitamin E has further been used to treat sickle cell anemia over a period of from 6 to 35 weeks; cf. Natt CL. Am. J. Clin. 33, pp. 968-971 (1980); Natt CL. Am. J. Clin. Nutr. 32, pp. 1359-1362 (1979); Gawlik G.M. Fed. Proc. 35 (3), p. 252 (1976); and Gorash L. Bieri J.G. et al., Univ. Conn. Farmington, CT.

It has further been known that a daily dose of 750 mg of vitamin E over a period of from 3 to 6 months was successfully used to treat thalassemia patients, whereupon a normalization of the hemolysis of the erythrocytes was observed; cf. Kahane I. ISR. J. Med. 12 (1), pp. 11-15 (1976).

Vitamin E has further been successfully applied to patients suffering from an acute hepatitis or an alcoholic hepatitis who have a vitamin E definciency in serum; cf. Yoshiakawa T., Takemura S., Kato H. et al., Japan. J. Gastrovent, 74/7, pp. 732-739 (1977). Moreover, vitamin E has been used to treat patients suffering from iron deficiency anemia, in which treatment vitamin E caused in improvement or normalization of the lipid metabolism in the bone marrow to occur in the course of from 4 to 8 weeks; cf. Takoshi Itaga, Central Clinical Laboratory Nagasaki University of Medicine, Japan.

It has now surprisingly been found that combinations comprising vitamin E and vasodilators and/or blood circulation promoters are suitable for the treatment of rheumatic diseases. This new range of indictions was not foreseeable from the state of the art and opens a new wide field of applications for vitamin E.

SUMMARY OF THE INVENTION

Thus, it is an object of the present invention to provide agents containing vitamin E for the treatment of rheumatic diseases. These agents may be formulations for external and internal applications.

It is another object of the present invention to provide anti-rheumatic agents that contain vitamin E in combination with blood circulation promoters, more specifically those promoting blood circulation in the skin region, and/or other vasodilators.

The term "rheumatic diseases" is understood to denote the pain and restrictions to motion. There is a variety of causes therefor such as, e.g. cephalgia, brachialgia, lumbago, cardialgia, nephralgia, myalgia, and also neuralgiae, pains in the regions of the peripheral nerves. For purposes of the present invention, "rheumatic diseases" is intended to have the general meaning as given above, that is, a disease causing pain and restrictions to motion.

DETAILED DESCRIPTION OF THE INVENTION

It has surprisingly been found that the action of vitamin E is significantly increased in the presence of vasodilators and/or blood circulation-promoting agents, and thereby the duration of treatment is shortened. The symptoms of the diseases will be more rapidly reduced. However, the combination preparations containing vitamin E will have to be administered for an extended period of time, that is, for about 6 months or more.

Also unexpectedly, the penetration of vitamin E through the skin is also particularly increased by the presence of agents promoting blood circulation such as heparin sodium, Extract. Hippocastani etc., whereby the effect of vitamin E is significantly enhanced. When heparin sodium is used, a high dose of from 30,000 to 150,000 I.U. is preferred.

It has been found that upon application of the active substances (vasodilators and/or blood circulation-promoting agents) in combination with a sufficient dose of vitamin E, the duration of the treatment can be substantially shortened. The symptoms of the disease will be faster reduced so that after some time the dosages to be applied can be lowered.

These results were not foreseeable and enable a therapy wherein part of the active chemical is replaced by a substance of natural origin which substance, moreover, is substantially present in every cell of the body.

Agents that will essentially increase the action of vitamin E and, hence, can be used in the present invention are agents promoting the blood circulation such as Extract. Hippocastani, $\beta$-hydroxyethylrutoside, Extract. Arnicae, nicotinic acid, nicotinic acid ester and deriviatives thereof, xanthinol nicotinate, inositol nicotinate, and salicylic acid or the esters thereof, dihydroergotoxine methanesulfonate, dihydroergocornine methanesulphonate, dihydroergocristine methanesulphonate and $\beta$-hydroxyethylsalicylate. It has now been found that upon application of these agents in combination with a sufficient dose of vitamin E, the symptoms in many patients will be faster reduced and, after some months, the amounts of these blood circulation promoters can be lowered.

In addition to the aforementioned vasodilators and blood circulation promoters, other similar products such as cinnarizine, vincamine etc. may also be used.

Combinations according to the invention containing sufficient amounts of vitamin E also improve the blood circulation in the extremities, of the eye periphery, of the inner ear and of the cerebrum. If, in addition, dimethylaminoethanol is added to the combinations according to the invention, the blood circulation in the brain, the stimulation of the central nervous system, and the concentrating ability are enhanced. The efficacy of vitamin E in cases of the respective indications is particularly surprising and allows vitamin E to be used in further new fields of application.

In oral anti-rheumatic agents, above all, a sufficient dosage of vitamin E which should be at least 150 mg as this amount is crucial for the efficacy of vitamin E in combination with vasodilators and/or blood circulation-promoting agents. Lower dosages of vitamin E are useless, since large parts thereof are destroyed by the gastric acid and thereby lose their activity; cf. Arthur Vogelsang, in Angiology 21, pp. 275–279 (1970).

If, in the past, sometimes low amounts of vitamin E, viz. up to 40 mg, have been employed in combination preparations, these amounts with certainty were ineffective due to the low doses. For the treatment of rheumatic diseases, the dosage of vitamin E should be in the range of from 150 to 600 mg. Preferably dosage forms containing from 150 to 500 mg of vitamin E are used. Typical combination preparations contain 200 to 400 mg of vitamin E. More specifically, in the combination containing nicotinic acid there are required high vitamin E doses of between 300 and 500 mg per dosage unit.

In the oral dosage form, there may be employed as the vitamin E the ester of natural origin or of synthetic origin as well as the free tocopherol. In the antirheumatic ointment or gel or cream, respectively, only the free tocopherol, such as D,L-alpha-tocopherol is used.

The agents according to the invention contain the conventional carriers and excipients in addition to vitamin E and the other active ingredients. Since vitamin E is liquid at normal temperatures, soft gelatin capsules particularly offer themselves as a suitable application form. The other active ingredients are incorporated in the vitamin E and, if desired, in a low-viscosity neutral oil and a solutizer in a per se known manner. In this step suitable emulsifiers, e.g. Tween, may be employed. More specifically, there may be used the standard recipes of the firm Scherer, Eberbach, West Germany. The application in the form of drops, e.g. as an alcoholic solution, of the combination according to the invention may also be suitable.

More particularly, successful results have been obtained in the treatment of rheumatic diseases by applying suppositories containing vitamin E. However, in the various fields of use and applications, the suitable additives for assisting in the treatment had to be selected. The conventional excipients and carriers can be employed for formulating suppositories. Nevertheless, suppositories containing high doses of vitamin E alone can also be used for the treatment of rheumatic diseases.

The combination with blood circulation promoting agents such as, e.g., Extract. Hippocastani or β-hydroxyethyl rutoside or rutoside derivatives containing several hydroxyethyl groups, respectively, can be used. Nicotinic acid or its esters or derivatives such as, e.g., nicotinic acid benzylester or nicotinic acid β-hydroxyethylester etc., may be beneficial and may enhance the effect caused by vitamin E and shorten the process of healing. The advantage of using suppositories resides in that vitamin E is not destroyed by the action of gastric acid. The resorption is increased by the use of emulsifiers such as, e.g., oleic acid alkyl ester.

As the conventional bases for ointments or creams, there may be used Eucerin cum aqua, Ungentum Cordes or Ungentum emulsificans as well as other water-insoluble ointment bases and mixtures thereof. For example, suitable ointment bases are wool wax, petrolatum DAB 8, highly fluid paraffin, and mixtures thereof. They may also contain emulsifiers such as cetylstearylalcohol.

Also suitable as bases for ointments are Unguentum alcoholum lanae aquosum containing about 5 to 10% of Cetiol (oleyl oleate) and Unguentum lanette, 24 parts of cetylstearylalcohol, 16 parts of Cetiol DAB 8, and 60 parts of Aqua conservata.

When such a combination is applied, the vitamin E will readily penetrate into the skin. Of course, further vitamins such as those of the B complex, e.g. $B_1$, $B_2$ and compatible anodynes such as local anesthetics may be added. Local anesthetics are vasodilators. They may be added to the ointments as a surface anesthetic such as Anaesthesin (Ethaforum) or Tetracain (Pantocain) or they may be incorporated into the capsules such as Procain or Procain hydrochloride, respectively.

The present invention further describes antirheumatic agents for external applications such as, e.g., a cream, a gel, an ointment or a lotion containing vitamin E.

Such an ointment contains the following components: 70 to 30% by weight, preferably 60 to 40% by weight, of water, 30 to 5% by weight, preferably 25 to 7% by weight, of Cetiol (oleyl oleate), and 30 to 2% by weight, preferably 25 to 2% by weight, of cetylstearylalcohol or other aliphatic alcohols.

In the place of the cetylstearylalcohol, there may also be used, altogether or in part, other emulsifying alcohols, such as, e.g., aliphatic alcohols or wool wax alcohols or diols, respectively, stearinol, monoglycerides esterified with aliphatic acids or similar substances. There may also be added, e.g., paraffin or petrolatum or other suitable materials in order to render the ointment spreadable. Cetiol (oleyl oleate) may also be completely or partially replaced by other emulsifiers such as Tween 20 or Tween 80 etc. It has been found that a particularly preferred combination as a base for ointments or creams containing vitamin E is as follows:

30 to 20% by weight of cetylstearylalcohol,
20 to 10% by weight of Cetiol (oleyl oleate),
60 to 40% by weight of water (aqua conservata).

This ointment containing vitamin E will be immediately absorbed into the skin.

It has been known that ointment bases containing water such as Ungentum emulsificans aquosum and Unguentum alcoholum lanae aquosum are suitable for processing water-soluble active substances. However, it is surprising that ointment bases containing water to an amount of approximately more than 50% are very well suitable for processing lipophilic active substances such as vitamin E. As the skin-stimulants or skin blood circulation-promoters there are to be mentioned, for example, 0l. juniperi, 0l. pini pumilionis (dwarf pine oil), 0l. eucalypti, 0l. rosmarinae, Tinct. camphorae (or camphor, respectively).

As vegetable vasodilators there are to be mentioned, e.g., Extract. calendulae from the flower and Herba calendulae. It has been determined that these vasodilators or blood circulation-promoters, respectively, significantly increase the effect of vitamin E and/or shorten the duration of the treatment, respectively, and remove the pain at long sight. At long sight, also the use of vitamin E also causes stabilization to be achieved and the symptoms to be permanently removed, so that the probability of a relapse will be very low.

There may also be used further derivatives of the blood circulation-promoting or vasodilators, respectively, e.g. trimethylol rutoside.

It has also unexpectedly been found that the antirheumatic agents according to the present invention are particularly beneficial if these medicaments additionally contain vitamin A. More specifically, the duration of the treatment will be shortened. Thus, the invention includes those anti-rheumatic medicaments that contain the vitamins A and E and blood circulation-promoting agents.

Vitamins A and E very strongly tend to clog in an aqueous medium, more particularly so in the presence of other active substances. Thus, it may happen that the lipophilic valuable substances are not absorbed.

It has now been determined that surprisingly small amounts of about 1% of an emulsifier are sufficient to prevent clogging. The active substances are more readily dispersed or suspended, respectively, in the aqueous medium. This is advantageous in that the absorption by the intestine is facilitated. A higher amount of emulsifier is not necessary, as in most cases 1 to 7% will suffice to prevent clogging. Emulsifiers may be used in amounts up to 10% or even more, but these larger amounts have the drawback that side-effects may possibly occur when the medicament is taken over an extended period of time.

Conventional emulsifiers as used in medical preparations can be employed, such as Tween 20, Cremophor ®, aliphatic alcohols, partially esterified triglycerides etc. However, in the present invention Tween 80 and Cetiol are preferred. It has been observed that, upon the addition of about 10% of emulsifier, the emulsification is not substantially improved over that effected by the addition of 5% of emulsifier.

Lecithin in a concentration between 1 and 13% may also be used as emulsifier. This favors the resorption of the combination of vitamins A and E and more specifically the resorption of vitamin A. Small amounts of lecithin will suffice to prevent clogging of the lipophilic vitamins and to positively affect the optimal resorption. Although upon the use of large amounts of lecithin, up to 50%, a positive effect is determinable, it is recommended to add about 1% of a conventional emulsifier such as Tween 80, as thereby, the miscibility of lecithin with the two other vitamins is positively affected and clogging is prevented. With respect to the resorption properties, the use of conventional emulsifiers such as, e.g. Tween 80, in an amount of about 1% together with from 1 to 13% of lecithin is particularly beneficial. There may also be used Tween 20, Cetiol (oleyl oleate) and Cremophor ® types. As the lecithin preparation, soybean lecithin is preferred.

Vitamin E can be used in any of its alpha forms, as free tocopherol or as an ester thereof. The ester may be an acetate, succinate or any other acceptable ester. Dosage forms such as tablets and dragees using vitamin E in the solid state may be prepared. It may also be administered in an alcoholic solution. Vitamin E is preferred to be administered in a high quantity per dosage unit, if possible between 200 and 600 mg and preferably between 300 and 500 mg.

Vitamin A can be employed as vitamin A palmitate, vitamin A acetate, a further ester of vitamin A or as beta-carotene.

The amount of vitamin A in the dosage unit is to be selected so that the maximum daily dose will not exceed 50,000 I.U., i.e. when two dosage units are to be administered per day, the dosage unit should contain a maximum of 25,000 I.U.

Further additives such as, e.g., vitamins of the B series or analgesics etc. may be included. For example, as the agents promoting blood circulation, there may be used the following substances or derivatives thereof: Inositol nicotinate, nicotinic acid, Cinnarizine, Bencyclan hydrogen fumarate, Vincamine, dihydroergotoxine methanesulphonate, Pentoxifylline, beta-pyridylcarbinol, Bamethan sulfate, Gingko flavoglycosides, beta-hydroxyethylrutoside, and Extract. Hippocastani.

The agents promoting blood circulation may also be used in their retard forms (sustained release drugs).

Combinations according to the present invention containing sufficient amounts of vitamin E also improve the blood circulation in the extremities, the periphery of the eye, the inner ear, and the cerebrum. The activity of vitamins A and E in the cases of these indications is particularly surprising and will open further new fields of applications for these vitamins. Numerous blood circulation-promoting agents such as hydroxyrutosides also have anticoagulant properties.

In anti-rheumatic plasters, vitamin E is added in the form of D-alpha-tocopherol or D,L-alpha-tocopherol in an amount of from 0.02 to 4 g, and preferably from 0.1 to 3 g. The combination with vasodilators such as Extract. Arnicae and with blood circulation promoters such as Extract. Hippocastani or Extract. Capsicae and with pain-alleviating drugs such as Extract. Belladonnae is preferred.

The present invention is further illustrated by the following non-limiting examples showing typical combinations of active substances and dosages.

EXAMPLE 1

There can be prepared 100 g of an ointment containing
400 mg of allantoin;
400 mg of Dexapanthenol;
5,000 mg of D-alpha-tocopherol; and
30,000 I.U. of heparin sodium.

EXAMPLE 2

There can be prepared 100 g of an ointment containing
2.5 g of O-(β-hydroxyethyl) rutoside and
6.5 g of D-alpha-tocopherol or D,L-alpha-tocopherol.

EXAMPLE 3

There can be prepared 100 g of an ointment containing
400 mg of allantoin;
400 mg of Dexapanthenol;
8.8 g of D-alpha-tocopherol or D,L-alpha-tocopherol; and
30,000 I.U. of heparin sodium.

EXAMPLE 4

There can be prepared 100 g of an ointment containing
4.5 g of Extract. Hippocastani (containing about 800 mg of escin) and
5.0 g of D-alpha-tocopherol.

EXAMPLE 5

There can be prepared 100 g of a gel containing
50,000 I.U. of heparin sodium;
12 g of Arnica flower extract ((1:10), alcohol 60%);
25 g Tinct. Hippocastani e sem. (1:1, equals 0.65 g of escin);

and
7.5 g of D-alpha-tocopherol.

EXAMPLE 6

There can be prepared 100 g of a gel containing
7.0 g of β-hydroxyethyl salicylate and
7.0 g of D-alpha-tocopherol.

EXAMPLE 7

A plaster (15 cm×25 cm in size) for rheumatic disease treatment can be prepared containing on one side thereof
70 mg of Extract. Arnicae;
70 mg of Extract. Capsici;
30 mg of Extract. Belladonnae; and
1500 mg of D-alpha-tocopherol concentrate.

EXAMPLE 8

There can be prepared 100 g of an ointment containing
10 g of benzocain (anesthesin);
8 g of D-alpha-tocopherol-concentrate; and
1 g of benzyl nicotinate.

EXAMPLE 9

There can be prepared 100 g of an ointment containing
3 g of β-hydroxyethyl salicylate;
1 g of benzyl nicotinate; and
7 g of D-alpha-tocopherol.

EXAMPLE 10

There can be prepared 100 g of an ointment containing
8 g of D-alpha-tocopherol;
400 mg of allantoin;
400 mg of Dexapanthenol; and
150,000 I.U. of heparin sodium.

EXAMPLE 11

There can be prepared, capsules each containing
250 mg of nicotinic acid;
400 mg of D,L-alpha-tocopherol acetate; and
150 mg of soybean oil.

EXAMPLE 12

There can be prepared, capsules each containing
200 mg of β-hydroxyethyl rutoside;
300 mg of D,L-alpha-tocopherol acetate; and
180 mg of soybean oil.

EXAMPLE 13

There can be prepared, capsules each containing
150 mg of Extract. Hippocastani (containing 25 mg of escin);
300 mg of D,L-alpha-tocopherol acetate; and
150 mg of soybean oil.

EXAMPLE 14

There can be prepared, capsules each containing
300 mg of xantinol nicotinate;
400 mg of D-alpha-tocopherol; and
190 mg of soybean oil.

EXAMPLE 15

There can be prepared, capsules each containing
150 mg of Extract. Hippocastani (containing 25 mg of escin);
250 mg of vitamin E; and
150 mg of soybean oil.

EXAMPLE 16

There can be prepared, capsules each containing
5 mg of vitamin $B_1$;
5 mg of vitamin $B_2$;
5 mg of vitamin $B_6$;
200 mg of β-hydroxyethyl rutoside;
300 mg of vitamin E;
50 mg of nicotinic acid amide; and
200 mg of soybean oil.

EXAMPLE 17

There can be prepared, capsules each containing
100 mg of nicotinic acid;
100 mg of extract from horse-chestnuts (containing 16 mg of escin);
300 mg of D-alpha-tocopherol acetate; and
200 mg of soybean oil.

EXAMPLE 18

There can be prepared, capsules each containing
200 mg of inositol nicotinate;
300 mg of D-alpha-tocopherol concentrate; and
150 mg of soybean oil.

EXAMPLE 19

There can be prepared, capsules each containing
50 mg of procaine hydrochloride;
400 mg of D-alpha-tocopherol concentrate; and
150 mg of soybean oil.

EXAMPLE 20

There can be prepared, capsules each containing
50 mg of procaine hydrochloride;
400 mg of D,L-alpha-tocopherol acetate;
5 mg of vitamin $B_1$;
5 mg of vitamin $B_2$;
5 mg of vitamin $B_6$; and
150 mg of soybean oil or corn oil.

EXAMPLE 21

Drops can be prepared wherein 100 ml of 90% ethyl alcohol contain
40 g of D,L-alpha-tocopherol acetate and
4.5 g of Extract. Hippocastani (containing 750 mg of escin).

EXAMPLE 22

There can be prepared, capsules each containing
4.5 mg of dihydroergotoxine methanesulfonate and
400 mg of D,L-alpha-tocopherol acetate.

EXAMPLE 23

There can be prepared, capsules each containing
50 mg of procaine hydrochloride;
200 mg of nicotinic acid;
400 mg of vitamin E; and
150 mg of corn oil.

EXAMPLE 24

There can be prepared, capsules each containing
150 mg of bencyclane hydrogenfumarate;
400 mg of vitamin E as D,L-alpha-tocopherol acetate; and
150 mg of soybean oil.

EXAMPLE 25

Suppositories are prepared containing
450 mg of D-alpha-tocopherol concentrate;
30 mg of nicotinic acid benzyl ester;
100 mg of a dried, de-proteinated aqueous extract from Testis bovis;
70 mg of Extract. muirae pumae sicc.; and
2.0 g of Stadimol.

EXAMPLE 26

Suppositories are prepared containing
450 mg of D,L-alpha-tocopherol;
40 mg of Cetiol (oleic acid oleyl ester);
150 mg of zinc oxide; and
2.0 g of Stadimol.

EXAMPLE 27

Suppositories are prepared containing
400 mg of vitamin E;
200 mg of β-hydroxyethyl rutoside;
40 mg of Cetiol; and
and 2.0 g of Stadimol.

EXAMPLE 28

Suppositories are prepared containing
350 mg of vitamin E
250 mg of Extract. Hippocastani (containing about 80 mg of escin); and
2.0 g of Stadimol.

EXAMPLE 29

Suppositories were prepared in accordance with Example 27, however using
300 mg of vitamin E and
200 mg of Triethylol rutoside.

EXAMPLE 30

There can be prepared, capsules each containing

| | |
|---|---|
| Pentoxifyllin | 400 mg; |
| vitamin E | 400 mg; |
| vitamin A acetate | 15,000 I.U.; and |
| soybean oil | 120 mg. |

EXAMPLE 31

There can be prepared, capsules each containing

| | |
|---|---|
| Naftidirofuryl hydrogenoxalate | 100 mg; |
| vitamin E | 500 mg; |
| vitamin A palmitate | 30,000 I.U.; and |
| soybean oil | 150 mg. |

EXAMPLE 32

There can be prepared, capsules each containing

| | |
|---|---|
| Cinnarizine | 75 mg; |
| vitamin E | 400 mg; |
| vitamin A palmitate | 15,000 I.U.; |
| vitamins B$_1$, B$_2$, B$_6$ (in equal amounts) | 10 mg; |
| vitamin B$_{12}$ | 5 μg; and |
| soybean oil | 150 mg. |

EXAMPLE 33

There can be prepared 100 ml of drops containing in ethyl alcohol

| | |
|---|---|
| Cinnarizine | 7.5 g; |
| vitamin E | 4.0 g; and |
| vitamin A palmitate | 2,500,000 units. |

EXAMPLE 34

There can be prepared, capsules each containing

| | |
|---|---|
| xantinol nicotinate | 500 mg; |
| vitamin E (D,L-alpha-tocopherol) | 400 mg; |
| vitamin A palmitate | 10,000 I.U. |
| Tween 80 | 20 mg; and |
| soybean oil | 150 mg. |

EXAMPLE 35

There can be prepared 100 ml of drops containing in ethyl alcohol

| | |
|---|---|
| dihydroergotoxine methanesulfonate | 1.5 g (comprising) |
| 0.5 g of dihydroergocristine methanesulfonate, | |
| 0.5 g of dihydroergocornine methanesulfonate, | |
| 0.333 g of alpha-dihydroergocryptine methanesulfonate and | |
| 0.167 g of β-dihydroergocryptine methanesulfonate); | |
| vitamin E D,L-alpha-tocopherol acetate) | 3.5 g; and |
| vitamin A palmitate | 2,500,000 units. |

EXAMPLE 36

There can be prepared, capsules each containing

| | |
|---|---|
| β-pyridyl carbinol tartrate (conforming to 150 mg of pyridylcarbinol); | 360 mg |
| D-alpha-tocopherol acetate | 400 mg; |
| vitamin A palmitate | 12,000 I.U.; and |
| soybean oil | 150 mg. |

EXAMPLE 37

There can be prepared, capsules each containing

| | |
|---|---|
| DL-alpha-tocopherol | 400 mg; |
| β-hydroxyethyl rutoside | 300 mg; |
| vitamin A palmitate | 15,000 I.U.; and |
| soybean oil | 150 mg. |

EXAMPLE 38

There can be prepared, capsules each containing

| | |
|---|---|
| Gingko flavoglycosides | 3.0 mg; |
| vitamin E DL-alpha-tocopherol acetate | 300 mg; |
| vitamin A palmitate | 25,000 I.U.; and |
| soybean oil | 100 mg. |

EXAMPLE 39

There can be prepared, capsules each containing

| | | |
|---|---|---|
| nicotinic acid | 300 | mg; |
| vitamin E | 400 | mg; |
| vitamin A palmitate | 15,000 | I.U.; |
| Cetiol (oleylic acid ester) | 20 | mg; and |
| soybean oil | 150 | mg. |

EXAMPLE 40

There can be prepared, capsules each containing

| | | |
|---|---|---|
| DL-alpha-tocopherol acetate | 400 | mg; |
| β-Hydroxyethylrutoside | 300 | mg; |
| vitamin A palmitate | 25,000 | I.U.; and |
| soybean oil | 120 | mg. |

EXAMPLE 41

There can be prepared, capsules each containing

| | | |
|---|---|---|
| Pentoxifylline | 400 | mg; |
| vitamin E DL-alpha-tocopherol acetate | 400 | mg; |
| vitamin A palmitate | 15,000 | I.U.; |
| Tween 80 | 10 | mg; and |
| soybean oil | 150 | mg. |

EXAMPLE 42

There can be prepared, capsules each containing

| | | |
|---|---|---|
| Bamethane sulfate | 25 | mg; |
| DL-alpha-tocopherol acetate | 250 | mg; |
| vitamin A palmitate | 10,000 | I.U.; and |
| soybean oil | 150 | mg. |

EXAMPLE 43

There can be prepared, capsules each containing

| | | |
|---|---|---|
| Vincamine | 30 | mg; |
| vitamin E DL-alpha-tocopherolacetate | 400 | mg; |
| vitamin A palmitate | 30,000 | I.U.; and |
| soybean oil | 150 | mg. |

EXAMPLE 44

An ointment can be prepared containing
10 g of D-alpha-tocopherol;
50,000 I.U. of heparin sodium; and
100 g of an ointment base comprising
22 parts of cetylstearylalcohol;
18 parts of Cetiol; and
60 parts of water.

EXAMPLE 45

An ointment can be prepared containing
7 g of vitamin E (D-alpha-tocopherol);
1 g of nicotinic acid benzyl ester;
1 g of camphor; and
100 g of an ointment base comprising
17 parts of cetylstearylalcohol;
8 parts of white petrolatum;
15 parts of Cetiol; and
60 parts of water (aqua conservata).

EXAMPLE 46

An ointment can be prepared containing
7 g of vitamin E;
15 g of Tinct. calendualae; and
100 g of an ointment base comprising
13 parts of wool wax alcohol;
2 parts of cetylstearylalcohol;
20 parts of Cetiol
5 parts of paraffin; and
50 parts of water (aqua conservata).

EXAMPLE 47

An ointment can be prepared containing
8 g of vitamin E (DL-alpha-tocopherol);
1.5 g of rosemary oil;
1 g of Extract. Hippocastani (standardized to at least 8% of escin);
1 g juniper oil; and
100 g of the ointment base of Example 44.

EXAMPLE 48

A solution can be prepared comprising
10 g of vitamin E (D-alpha-tocopherol concentrate);
1 g of dwarf pine oil (ol. pini pumilionis);
1 g of eucalyptus oil;
1 g of juniper oil; and
100 g of isopropyl alcohol.

EXAMPLE 49

An ointment can be prepared containing
7 g of D-alpha-tocopherol concentrate;
2 g of Tinct. arnicae;
2 g of salicylic acid β-hydroxyethyl ester; and
100 g of the ointment base of Example 44.

EXAMPLE 50

A solution similar to that in Example 48 can be prepared containing
7.0 g of vitamin E;
1.0 g dwarf pine oil;
1.0 g Tinct. arnicae; and
100 g of isopropyl alcohol.

EXAMPLE 51

An ointment can be prepared containing
9.0 g of vitamin E;
20.0 g Tinct. calendulae; and
100 g of the ointment base of Example 44.

The following Examples 52 through 66 relate to combinations of vitamins E and A with lecithin.

EXAMPLE 52

There can be prepared, capsules each containing

| | | |
|---|---|---|
| Pentoxifylline | 400 | mg; |
| vitamin E (D,L-alpha-tocopherol acetate) | 400 | mg; |
| vitamin A acetate | 25,000 | I.U.; |
| soybean lecithin | 200 | mg; |
| soybean oil | 120 | mg; and |
| Tween 80 | 8 | mg. |

EXAMPLE 53

There can be prepared, capsules each containing

| | |
|---|---|
| Naftidrofuryl hydrogenoxalate | 100 mg; |
| vitamin E (D-alpha-tocopherol-concentrate) | 500 mg; |
| vitamin A palmitate | 30,000 I.U. |
| soybean lecithin | 25 mg; and |
| soybean oil | 150 mg. |

EXAMPLE 54

There can be prepared, capsules each containing

| | |
|---|---|
| Cinnarizine | 75 mg; |
| vitamin E (D-alpha-tocopherol acetate) | 400 mg; |
| vitamin A palmitate | 25,000 I.U.; |
| vitamins $B_1$, $B_2$, $B_6$ (in equal amounts) | 10 mg; |
| vitamin $B_{12}$ | 5 µg; |
| soybean oil | 100 mg; and |
| soybean lecithin | 280 mg. |

EXAMPLE 55

There can be prepared 100 ml of drops containing in ethyl

| | |
|---|---|
| alcohol Cinnarizine | 7.5 g; |
| vitamin E | 4.0 g; |
| vitamin A palmitate | 2,500,000 I.U.; and |
| lecithin | 2.5 g. |

EXAMPLE 56

There can be prepared, capsules each containing

| | |
|---|---|
| Xantinol nicotinate | 500 mg; |
| vitamin E (DL-alpha-tocopherol) | 400 mg; |
| vitamin A palmitate | 25,000 I.U.; |
| Tween 80 | 20 mg; |
| soybean oil | 150 mg; and |
| soybean lecithin | 25 mg. |

EXAMPLE 57

There can be prepared 100 ml of drops containing in ethyl alcohol

| | |
|---|---|
| dihydroergotoxine methanesulfonate | 1.6 g (comprising) |
| 0.5 g of dihydroergocristine methanesulfonate, | |
| 0.5 g of dihydroergocornine methanesulfonate, | |
| 0.333 g of alpha-dihydroergocryptine methanesulfonate and | |
| 0.167 g of β-dihydroergocryptine methanesulfonate); | |
| vitamin E (DL-alpha-tocopherol acetate) | 3.5 g; |
| vitamin A palmitate | 1,500,000 I.U.; and |
| soybean lecithin | 3.5 g. |

EXAMPLE 58

There can be prepared, capsules each containing

| | |
|---|---|
| β-pyridyl carbinol tartrate corresponding to 150 mg of pyridyl carbinol; | 360 mg |
| D-alpha-tocopherol acetate | 400 mg; |
| vitamin A palmitate | 10,000 I.U.; |
| soybean oil | 100 mg; |

-continued

| | |
|---|---|
| soybean lecithin | 150 mg; and |
| Tween 20 | 6 mg. |

EXAMPLE 59

There can be prepared, capsules each containing

| | |
|---|---|
| DL-alpha-tocopherol | 400 mg; |
| β-hydroxyethyl rutoside | 300 mg; |
| vitamin A palmitate | 30,000 I.U.; |
| soybean oil | 100 mg; and |
| soybean lecithin | 250 mg. |

EXAMPLE 60

There can be prepared, capsules each containing

| | |
|---|---|
| Gingko flavoglycosides | 3.0 mg |
| vitamin E (D,L-alpha-tocopherol acetate) | 300 mg |
| vitamin A palmitate | 25,000 I.U.; |
| soybean oil | 100 mg; and |
| soybean lecithin | 200 mg. |

EXAMPLE 61

There can be prepared, capsules each containing

| | |
|---|---|
| nicotinic acid | 300 mg; |
| vitamin E | 400 mg; |
| vitamin A palmitate | 15,000 I.U.; |
| Cetiol (Oleic acid ester) | 10 mg; |
| soybean oil | 100 mg; and |
| soybean lecithin | 20 mg. |

EXAMPLE 62

There can be prepared, capsules each containing

| | |
|---|---|
| D-alpha-tocopherol | 200 mg; |
| lecithin | 500 mg; |
| soybean oil | 180 mg; and |
| Tween 80 | 10 mg. |

EXAMPLE 63

There can be prepared, capsules in accordance with Example 62 but additionally containing 15,000 I.U. vitamin A palmitate.

EXAMPLE 64

There can be prepared, capsules in accordance with Examples 62 and 63 but containing D,L-alpha-tocopherol acetate instead of D-alpha-tocopherol.

EXAMPLE 65

There can be prepared, capsules each containing

| | |
|---|---|
| D-alpha-tocopherol | 400 mg; |
| lecithin | 400 mg; |
| soybean oil | 200 mg; and |
| Tween 80 | 15 mg. |

EXAMPLE 66

There can be prepared, capsules in accordance with Example 65 but additionally containing 15,000 I.U. vitamin A palmitate or vitamin A acetate or 9.5 mg β-carotene.

The products shown in Examples 52 through 66 can be used as agents for lowering the cholesterol level.

The following Examples 67 through 95 relate to the additional use of dimethylaminoethanol in the combinations according to the present invention.

EXAMPLE 67

There can be prepared a formulation containing
20 mg of dimethylaminoethanol;
400 mg of D,L-alpha-tocopherol acetate;
12,000 I.U. of vitamin A palmitate (6.67 mg);
50 mg of soybean oil;
200 mg of soybean lecithin; and
200 mg of β-hydroxyethylrutoside.

EXAMPLE 68

There can be prepared a formulation containing
20 mg of dimethylaminoethanol;
400 mg of D,L-alpha-tocopherol acetate;
12,000 I.U. of vitamin A palmitate (6.67 mg);
100 mg of soybean oil;
300 mg of lecithin; and
75 mg of Cinnarizine.

EXAMPLE 69

There can be prepared a formulation containing
25 mg of dimethylaminoethanol orotate;
400 mg of D,L-alpha-tocopherol acetate;
15,000 I.U. of vitamin A palmitate (8.33 mg);
20 mg of soybean lecithin; and
400 mg nicotinic acid.

EXAMPLE 70

There can be prepared a formulation as in Example 67, but additionally containing 8 mg of Tween 80.

EXAMPLE 71

There can be prepared a formulation containing
25 mg of dimethylaminoethanol orotate;
500 mg of D-alpha-tocopherol concentrate;
22,000 I.U. of vitamin A palmitate (12.22 mg);
28 mg of soybean lecithin;
120 mg of soybean oil; and
3.0 mg of Ginkoflavoglucoside

EXAMPLE 72

There can be prepared a formulation as in Example 71, but additionally containing 8 mg of Tween 20.

EXAMPLE 73

There can be prepared a formulation containing
30 mg of dimethylaminoethanol orotate;
400 mg of D,L-alpha-tocopherol acetate;
300 mg of lecithin;
8 mg of Tween 80; and
30 mg of Vincamine.

EXAMPLE 74

There can be prepared a formulation containing
25 mg of dimethylaminoethanol orotate;
350 mg of D-alpha-tocopherol acetate;
15,000 I.U. of vitamin A palmitate;
5 mg of each of the vitamins $B_1$, $B_2$, $B_6$;
5 μg of vitamin $B_{12}$;
15 mg of nicotinic acid amide;
280 mg of lecithin; and
75 mg Cinnarizine.

EXAMPLE 75

There can be prepared a formulation as in Example 74, but additionally containing 5 mg of Tween 80.

EXAMPLE 76

There can be prepared a formulation containing
25 mg of dimethylaminoethanol orotate;
400 mg of D,L-alpha-tocopherol acetate;
15,000 I.U. of vitamin A palmitate (8.33 mg); and
300 mg of β-hydroxyethylrutoside.

EXAMPLE 77

There can be prepared a formulation as in Example 76, but additionally containing 8 mg of Tween 80.

EXAMPLE 78

There can be prepared a formulation containing
35 mg of dimethylaminoethanol orotate;
500 mg of D-alpha-tocopherol concentrate;
22,000 I.U. of vitamin A palmitate (12.22 mg); and
400 mg of xantinol nicotinate.

EXAMPLE 79

There can be prepared a formulation as in Example 78, but additionally containing 4 mg of Tween 20.

EXAMPLE 80

There can be prepared a formulation containing
30 mg of dimethylaminoethanol orotate;
400 mg of D,L-alpha-tocopherol acetate; and
400 mg of Pentoxyfylline.

EXAMPLE 81

There can be prepared a formulation containing
35 mg of dimethylaminoethanol orotate;
350 mg of D-alpha-tocopherol acetate;
15,000 I.U. of vitamin A palmitate;
5 mg of each of the vitamins $B_1$, $B_2$ and $B_6$;
5 μg of vitamin $B_{12}$; and
100 mg of Bencyclane fumarate.

EXAMPLE 82

There can be prepared a formulation as in Example 81, but also containing 3 mg of Tween 80.

EXAMPLE 83

There can be prepared a formulation containing
25 mg of dimethylaminoethanol orotate;
350 mg of D,L-alpha-tocopherol acetate;
17,000 I.U. (9.44 mg) of vitamin A palmitate;
70 mg of soybean oil; and
75 mg of Cinnarizine.

EXAMPLE 84

There can be prepared a formulation containing
20 mg of dimethylaminoethanol;
200 mg of D,L-alpha-tocopherol acetate;
12,000 I.U. of vitamin A palmitate (6.67 mg);
50 mg of soybean oil; and
250 mg of soybean lecithin.

EXAMPLE 85

There can be prepared a formulation containing
35 mg of dimethylaminoethanol orotate;
400 mg of D,L-alpha-tocopherol acetate;
15,000 I.U. of vitamin A palmitate (8.33 mg); and
20 mg of soybean lecithin.

EXAMPLE 86

There can be prepared a formulation as in Example 84, but additionally containing 3 mg of Tween 80.

EXAMPLE 87

There can be prepared a formulation containing
20 mg of dimethylaminoethanol;
200 mg of D,L-alpha-tocopherol acetate;
12,000 I.U. of vitamin A palmitate (6.67 mg); and
50 mg of soybean oil.

EXAMPLE 88

There can be prepared a formulation containing
35 mg of dimethylaminoethanol orotate;
400 mg of D,L-alpha-tocopherol acetate; and
15,000 I.U. of vitamin A palmitate (8.33 mg).

EXAMPLE 89

There can be prepared a formulation as in Example 87, but additionally containing 3 mg of Tween 80.

EXAMPLE 90

There can be prepared a formulation containing
35 mg of dimethylaminoethanol orotate;
500 mg of D-alpha-tocopherol concentrate; and
22,000 I.U. of vitamin A palmitate (12.22 mg).

EXAMPLE 91

There can be prepared a formulation as in Example 90, but additionally containing 4 mg of Tween 20.

EXAMPLE 92

There can be prepared a formulation containing
30 mg of dimethylaminoethanol orotate; and
400 mg of D,L-alpha-tocopherol acetate.

EXAMPLE 93

There can be prepared a formulation containing
35 mg of dimethylaminoethanol orotate;
350 mg of D-alpha-tocopherol acetate;
15,000 I.U. of vitamin A palmitate;
5 mg of each of the vitamins $B_1$, $B_2$ and $B_6$;
5 μg of vitamin $B_{12}$; and
15 mg of nicotinic acid amide.

EXAMPLE 94

There can be prepared a formulation as in Example 93, but additionally containing 3 mg of Tween 80.

EXAMPLE 95

There can be prepared a formulation containing
25 mg of dimethylaminoethanol orotate;
350 mg of D,L-alpha-tocopherol acetate;
17,000 I.U. (9.44 mg) of vitamin A palmitate; and
70 mg of soybean oil.

In the Examples soybean oil was used, when present, in an amount of from 50 to 200 mg per capsule. However, other neutral oils such as olive oil, rape seed oil etc. can be used as well.

What is claimed is:

1. A method for treating rheumatic diseases in a patient suffering therefrom comprising administering to said patient vitamin E in an amount therapeutically effective to treat said rheumatic diseases in combination with a functionally effective amount of at least one of nicotinic acid or derivatives, Buflomedil, Flunarizine, Cinnarizine, Bencyclan hydrogenfumarate, Vincamine, dihydroergotoxine methanesulphonate, Pentoxifylline, beta-pyridylcarbinol, Bamethan sulfate, Gingko flavoglycosides, Extract. Hippocastani, and beta-hydroxyethylrutoside.

2. The method of claim 1, wherein vitamin E is administered in the form of a plaster containing D-alpha-tocopherol or D,L-alpha-tocopherol.

3. The method of claim 1, wherein a functional amount of vitamin A is included in the composition.

4. The method of claim 1, wherein vitamin E is administered in an amount of from 200–600 mg per unit dosage form.

5. The method of claim 1, wherein vitamin E is administered in an amount of from 300–500 mg per unit dosage form.

6. An anti-rheumatic pharmaceutical composition in capsule form, each capsule comprising an anti-rheumatic effective amount of vitamin E, lecithin, dimethylaminoethanol, in combination with a functionally effective amount of at least one of Cinnarizine, Bencyclan hydrogenfumarate, Vincamine, dihydroergotoxine methanesulphonate, Bamethan sulfate, beta-pyridylcarbinol, Extract. Hippocastani, Gingko flavoglycosides, beta-hydroxyethylrutoside, Flunarizine, and Buflomedil.

* * * * *